United States Patent
Molina

[19]
[11] Patent Number: 5,957,135
[45] Date of Patent: Sep. 28, 1999

[54] ARM HOLDER FOR TRANSILLARY FIRST RIB RESECTION

[75] Inventor: Jose Ernesto Molina, New Brighton, Minn.

[73] Assignees: Regents of the U. of Minnesota, Minneapolis, Minn.; Rultract, Inc., Cleveland, Ohio

[21] Appl. No.: 08/792,010

[22] Filed: Jan. 31, 1997

[51] Int. Cl.[6] .................................................. A61G 15/00
[52] U.S. Cl. ............................ 128/845; 128/846; 602/32
[58] Field of Search .................................. 128/845, 846, 128/878, 879, 882; 602/5, 32, 40

[56] References Cited

U.S. PATENT DOCUMENTS

| | | | |
|---|---|---|---|
| 1,048,750 | 12/1912 | Smith | 602/34 |
| 1,242,688 | 10/1917 | Hawley | 602/33 |
| 1,914,202 | 6/1933 | Henze | 602/32 |
| 3,403,675 | 10/1968 | Carr | 602/32 |
| 4,143,652 | 3/1979 | Meier . | |
| 4,622,955 | 11/1986 | Fakhrai . | |
| 4,702,465 | 10/1987 | McConnell . | |
| 5,088,472 | 2/1992 | Fakhrai . | |

OTHER PUBLICATIONS

Arch Surg, vol. 93. Jul. 1966 Thursday, Mar. 3, 1966. "Thoracic Outlet Syndrome" David B. Roos, M.D. and J. Cuthbert Annals of Surgery, Mar. 1966, "Transaxillary Approach for First Resection to Relieve Thoracic Outlet Syndrome", David B. Roos, M.D. pp. 354–358.

*Primary Examiner*—Michael A. Brown
*Attorney, Agent, or Firm*—Renner, Otto, Boisselle & Sklar

[57] ABSTRACT

A surgical support apparatus for a limb of a patient includes a support assembly, such as a sling, for supporting the limb during a surgical procedure, and a mounting assembly slidably coupled to the support assembly by at least one slide rod and at least one slide tube, the support assembly being vertically positionable relative to the mounting assembly. A method for supporting and positioning a patient's body part during surgery comprising the steps of attaching the body part to a sling or other support assembly, and adjusting the position of the body part by positioning the support assembly relative to a mounting assembly slidably coupled thereto, the mounting assembly including at least one slide rod and at least one slide tube to effect vertical positioning of the support assembly relative to the mounting assembly.

14 Claims, 5 Drawing Sheets

ARM HOLDER FOR TRANSILLARY FIRST RIB RESECTION

TECHNICAL FIELD

The present invention relates generally to surgical instruments for holding and elevating body parts during surgery, and more particularly to a surgical support apparatus for holding and elevating a patient's limb during transillary rib resection surgery.

BACKGROUND OF THE INVENTION

In the performance of thoracic, vascular and orthopedic surgery and related procedures, it is often necessary to support a portion of the patient's body including one or more limbs in a fixed position during the procedure, and also to vary the position from time to time. Oftentimes it is desirable to maintain such a limb, for example, in a fixed position during a surgical procedure so as to keep the procedure area as clear as possible and to avoid the limb interfering with the procedure. In some cases, operating room personnel manually support the particular extremity. For example, the assistant may have to stand on a platform in order manually to hold the arm at a right angle while the surgeon carries out the intervention. The patient usually is positioned in a lateral thoracotomy position with the arm elevated toward the ceiling at a right angle, and also with the forearm flexed at a right angle in relation to the arm.

Such use of operating room personnel to support manually a patient's extremity during a surgical procedure is undesirable in that the assistant becomes tired over time and finds it necessary to change position at a critical or otherwise inconvenient time. This may lead, for example, to actual trauma to the structures of the thoracic outlet due to the unusual excessive force. Furthermore, the assistant is unable to observe crucial aspects of the operation itself. Moreover, in addition to possibly interfering with the light available to the surgeon, the height of the assistant may increase the chances for contamination of the operating field.

It is well known and appreciated that in surgical procedures, time is of the essence, and delays associated with adjustments of support equipment are unwanted. Additionally, during certain procedures, it is desirable to impose or to change a biasing force on a body portion or limb which is undergoing a surgical procedure or treatment.

In view of the aforementioned shortcomings associated with conventional surgical techniques for supporting a patient's body part during surgery, there is a strong need in the art for a surgical support apparatus which may be mounted onto an operating table or be otherwise relatively secured and positioned outside the sterile field, and which affords for quick and easy positioning and repositioning of the patient's body part such as a limb for example.

SUMMARY OF THE INVENTION

The present invention provides a strong secured surgical support apparatus. The support apparatus affords for stable positioning of a patient's body part during surgery and allows for repositioning of it in a quick and smooth manner. The support apparatus is strong enough to support any size or weight human limb. The support apparatus is quickly and easily adjusted to a wide range of stable support positions. In particular, the support apparatus of the present invention includes at least one support bar that can be clamped to an operating table. The support bar is rotatable and affords for horizontal positioning of the patient's body part. A slide assembly is slidably coupled to the support bar and provides for transaxial positioning of the patient's body part relative to the support bar. The slide assembly also includes a cord assembly which provides for raising and lowering a hook bar which holds the patient's body part. Thus, the support apparatus of the present invention provides for quick and easy horizontal and vertical positioning of a patient's body part during surgery. As a result, the present invention affords among other things greater work space for a surgeon, a more sterile surgical environment, easier access to the patient, and avoidance of injury since the limb is held secured.

According to one aspect of the present invention, a surgical support apparatus for a limb of a patient is provided including: a support assembly for supporting the limb; and a mounting assembly slidably coupled to the support assembly by at least one slide rod and at least one slide tube. The support assembly being vertically positionable relative to the mounting apparatus.

In accordance with another aspect of the present invention, a method for supporting and positioning a patient's body part during surgery is provided including the steps of: attaching the body part to a support assembly; and adjusting the position of the body part by positioning the support assembly relative to a mounting assembly slidably coupled thereto, the mounting assembly including at least one slide rod and at least one slide tube to effect vertical positioning of the support assembly relative to the mounting assembly.

In accordance with yet another aspect of the invention, a surgical support apparatus for holding and elevating a body part during surgery is provided including: a support assembly for supporting the limb; and a mounting assembly slidably coupled to the support assembly by at least one slide rod and at least one slide tube, the support assembly being vertically positionable relative to the mounting apparatus, the mounting assembly also including a slide assembly and a support structure, the slide assembly being horizontally positionable along a hanger bar so as to provide for horizontal positioning of the support assembly to effect horizontal positioning of the limb, the support structure including a first portion vertically coupled to a second portion, the first portion being horizontal rotatable relative to the second portion so as to provide for positioning of the limb along a horizontal plane.

To the accomplishment of the foregoing and related ends, the invention then comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

DESCRIPTION OF THE PREFERRED EMBODIMENTS

Figure 1:
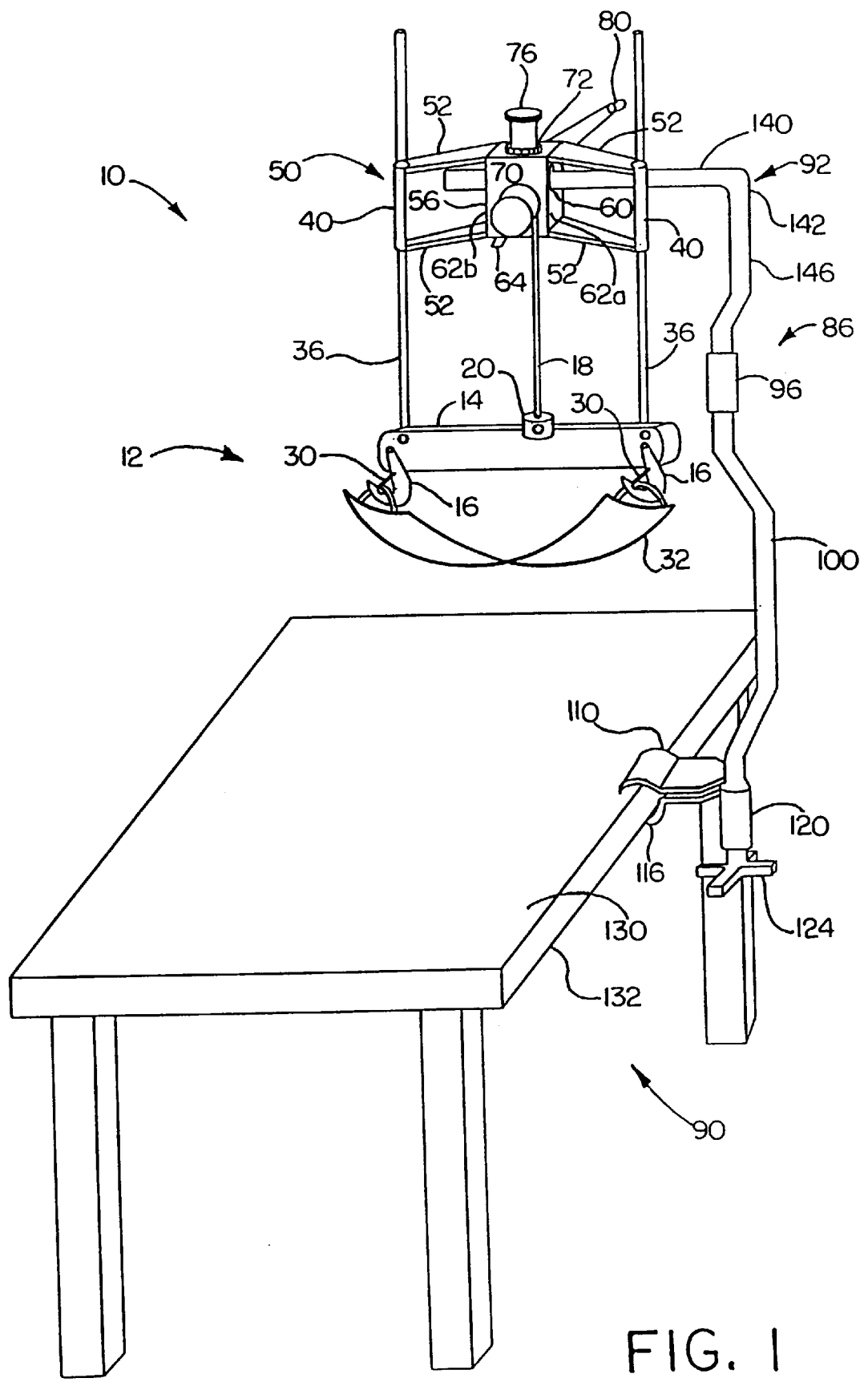
FIG. 1 is a perspective view of the support apparatus of the present invention mounted to a surgical operating table.

The present invention will now be described with reference to the drawings wherein like reference numerals are used to refer to like elements throughout. As mentioned above, the present invention relates to surgical instruments for holding and elevating body parts during surgery, and more particularly to a surgical support apparatus for holding and elevating a limb during transaxillary rib resection surgery.

Referring initially to FIG. 1, an exemplary embodiment of the limb holder is shown generally at 10. The limb holder includes a support assembly 12 for supporting a patient's limb. The support assembly includes a horizontally disposed hook bar 14—the hook bar 14 being transversely aligned with the surgical procedure surface. The hook bar is substantially rectangular in cross section and may be solid or hollow, as desired. Attached at each longitudinal end of the hook bar 14 are hooks 16. The hooks 16 function to secure the limb to the support assembly 12. Attached at the top center of the hook bar 14 is a cord 18 which is bolted to the hook bar 14 via a cord fastener 20. The function of the cord fastener 18 will be discussed in greater detail below.

Returning now to the hooks 16, each of the hooks 16 include a hook pin 30. The hook pins 30 serve to fasten whatever item is being secured to the hook 16. For example, a sling 32 may be used to hold a limb, the sling 32 being secured to the support assembly 12.

In the performance of various surgical procedures, particularly in orthopedic surgery, it may be necessary to support various portions (e.g., limbs) of the body including extremities in an elevated position during the surgical procedure. For example, the sling 32 attached to the support assembly 12 may be adapted to support an arm or leg of a patient at a suspended position while the procedure is performed. (Although the invention is described with respect to the supporting of an arm of a patient, it will be appreciated that the invention may be used to support other body parts, such as a leg, the head/neck, etc.) During such a procedure, it may be necessary to position the limb or to apply biasing forces in a particular direction. The support apparatus 10 of the present invention makes this possible because of the stability and ease of use provided by the support apparatus 10.

The support apparatus 10 affords for universally positioning of a limb secured in the sling 32. Moreover, the sling 32 is removable for quick and easy sterilization. The sling 32 may be removed by depressing the hook pins 30 and withdrawing the sling 32 from hooks 16.

If desired, the sling may be disposable. Also, if desired, the sling may be replaced by rings, straps or other devices for supporting the arm.

The hook pins 32 may include a spring bias (not shown) which provides for the hook pin 32 pivoting about an axis to allow an item such as the sling 32 to be fastened to the hook 16—the hook pin 32 springing back into a secure position once the item has been fastened on the hook 16.

Attached at each longitudinal end of the hook bar 14 are slide rods 36 which are perpendicularly bolted to the hook bar 14 via bolts 38. The slide rods are circular in cross section and may be solid or hollow, as desired. The slide rods 36 slidably sit through cylindrical slide tubes 40 at the slide assembly 50. The slide rods 36 in conjunction with the slide tubes 40 facilitate vertical positioning of the support assembly 12.

The slide assembly 50 includes support arms 52 which are each coupled to distal ends of the support tubes 40. The other end of the support arms 52 being coupled to the housing 56 of the slide assembly 50. The slide assembly housing 56 serves as a base for the slide assembly 50. Accordingly, the slide assembly housing 56, the support arms 52 which laterally protrude therefrom, and the slide tubes 40 vertically coupled at each distal end to a support arm 52 generally make up the frame of the slide assembly 50.

The slide assembly housing 56 includes orifices 60 through side walls 62. As will be discussed in greater detail below, the orifices 60 provide for horizontal positioning of the slide assembly 50. A gear lever 64 is shown protruding from the bottom side of the slide assembly housing 56. The gear lever 64 serves to lock the cord 18 so as to maintain the hook bar 14 at a desired vertical position. The cord 18 is coupled to a cord assembly 70. The cord assembly 70 is integral to the slide assembly housing 56, and serves to wind and release the cord 18 so as to effect vertical positioning of the hook bar 14.

The top surface of the slide assembly housing 56 includes a threaded sleeve 72 for receiving slide bolt 76 therethrough. A cord crank 80 is located on the back side of the slide assembly housing 56. The cord crank 80 serves to provide for winding or releasing the cord 18 via the cord assembly 70.

A support apparatus 86 provides for supporting the limb holder 10 relative to the work surface. In this exemplary embodiment the support apparatus 86 is shown mounted to an operating table 90. However, it will be appreciated that the support assembly 86 could be floor mounted, wall mounted, ceiling mounted or mounted to any suitable device or place. The support assembly 86 includes a hanger bar 92 which is slidably engaged with the slide assembly housing 56 through orifices 60. The orifices 60 are shaped so as to permit the slide assembly 50 to slide along the hanger bar 92. At the same time, the orifices 60 fit snugly around the perimeter of the hanger bar 92 so as to prevent play (i.e. loose fit) of the slide assembly 50 when sliding along the hanger bar 92.

A hanger sleeve 96 couples the hanger bar 92 to support bar 100. The hanger sleeve 96 serving as a coupling means is discussed in greater detail below in the discussion of FIGS. 3 and 4. Top clamps 110 is formed integral to the bottom portion of the support bar 100. A bottom clamp 116 is coupled to a clamp sleeve 120 which is slidably engaged to the bottom end of support bar 100. A clamp fastener 124 is threaded into the bottom vertical portion of the clamp sleeve 120. As will be discussed in greater detail with respect to FIGS. 3 and 4, the top and bottom clamps 110, 116 secure the limb holder 10 to the operating table 90 by clamping onto the top and bottom surfaces 130, 132 of the operating table 90.

Figure 3:
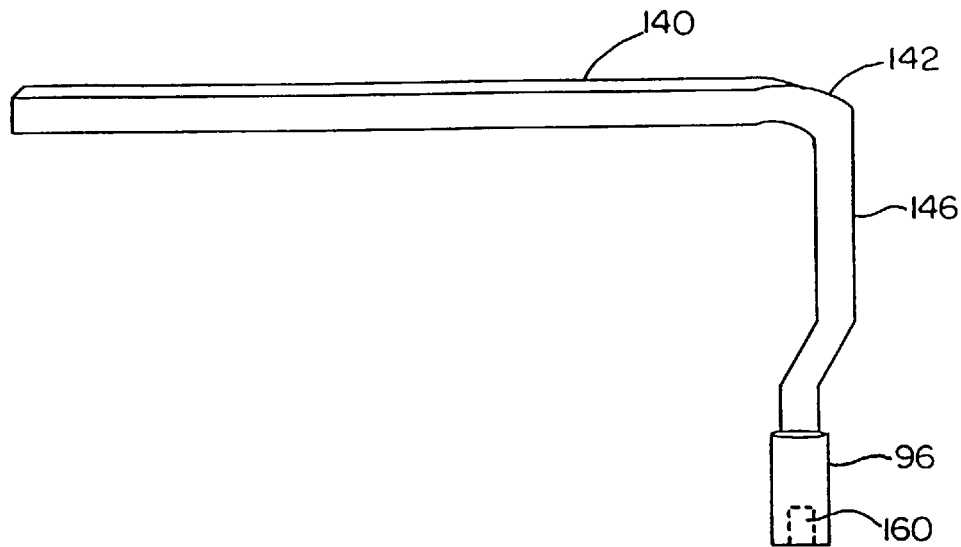
FIG. 3 is a perspective view of a hanger bar in accordance with the present invention.
Figure 4:
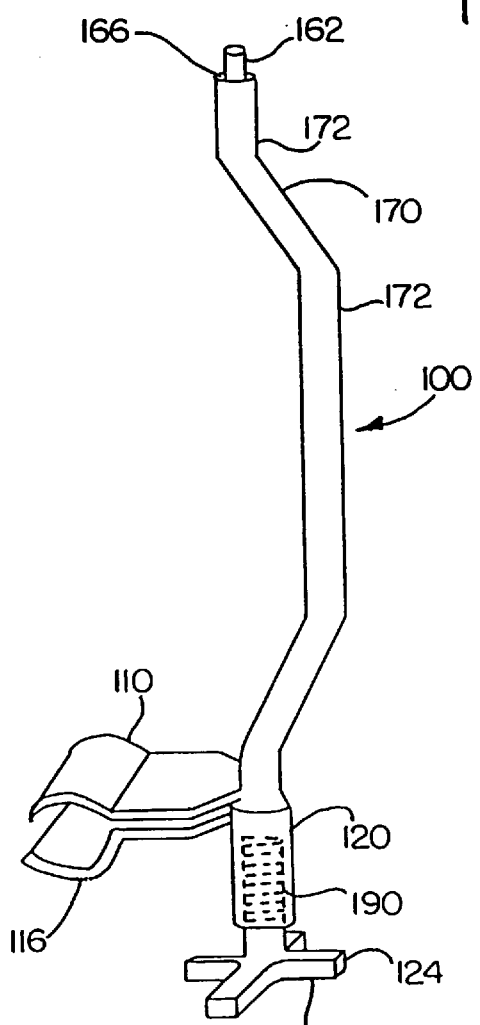
FIG. 4 is a perspective view of a support bar in accordance with the present invention.

Turning now to FIGS. 3 and 4, the hanger bar 92, hanger sleeve 96 and support bar 100 are shown in detail. The hanger bar 92 includes a horizontal portion 140 which as mentioned above the slide assembly 50 horizontally slides along via orifices 60. The horizontal portion 140 has a rectangular cross-sectional perimeter which ends into a near 90° bend 142. On the other end of the bend 142 is a vertical portion 146 which has a circular cross-sectional perimeter. The vertical portion 146 bends at is lower end in a S-shaped manner into the hanger sleeve 96. The bottom end of the hanger sleeve 96 includes a pin receiving cavity 160. The pin receiving cavity 160 receives pin 162 which protrudes from the upper surface 166 of support bar 100. The pin 162 is cylindrically shaped and fits snugly into the cylindrical pin receiving cavity 160. The pin 162 and cavity 160 provide for quick and easy coupling of the hanger bar 146 to the support bar 100. Additionally, the pin 162 and cavity 160 afford for rotatable positioning of the hanger bar 92 with respect to support bar 100. The support bar 100 is substantially C-shaped at its center. The C-shape affords for bringing the support bar 100 farther away from the operating table 90 and thus affords for increased operating space.

The C-shape is effected by a first vertical portion 170 bending outwardly into the top bend of second vertical portion 172 which bends inwardly at its bottom end into a second bend. Top clamp 110 protrudes perpendicularly outwardly from the bottom end of the support bar 100. The top clamp 110 may be welded to the support bar 100 or it may be die cast with support bar 100 as a single piece. Any suitable means for integrally attaching the top clamp 110 to the support bar 100 may be employed.

The bottom claim 116 is attached to the top portion of clamp sleeve 120. The bottom clamp 116 may be welded to the clamp sleeve 120 or it may be die cast with the clamp sleeve 120 as a single piece. Any suitable means for integrally attaching the bottom clamp 116 to the clamp sleeve 120 may be employed.

The clamp sleeve 120 is slidably coupled onto the bottom portion of the support bar 100. The threaded clamp fastener 124 includes a threaded end which screws into a threaded cavity 190 of the support bar 64. As the clamp fastener 124 is screwed into the threaded cavity 190, it raises upwardly the clamp sleeve 120 relative to the support bar 100. As a result, the bottom clamp 116 is brought closer to top clamp 110 to effect a clamping force on the top and bottom surfaces 130, 132 of the operating table 90. The clamp fastener 124 includes a cross-shaped handle 192 to facilitate screwing and unscrewing the claim fastener 124.

Figure 2:
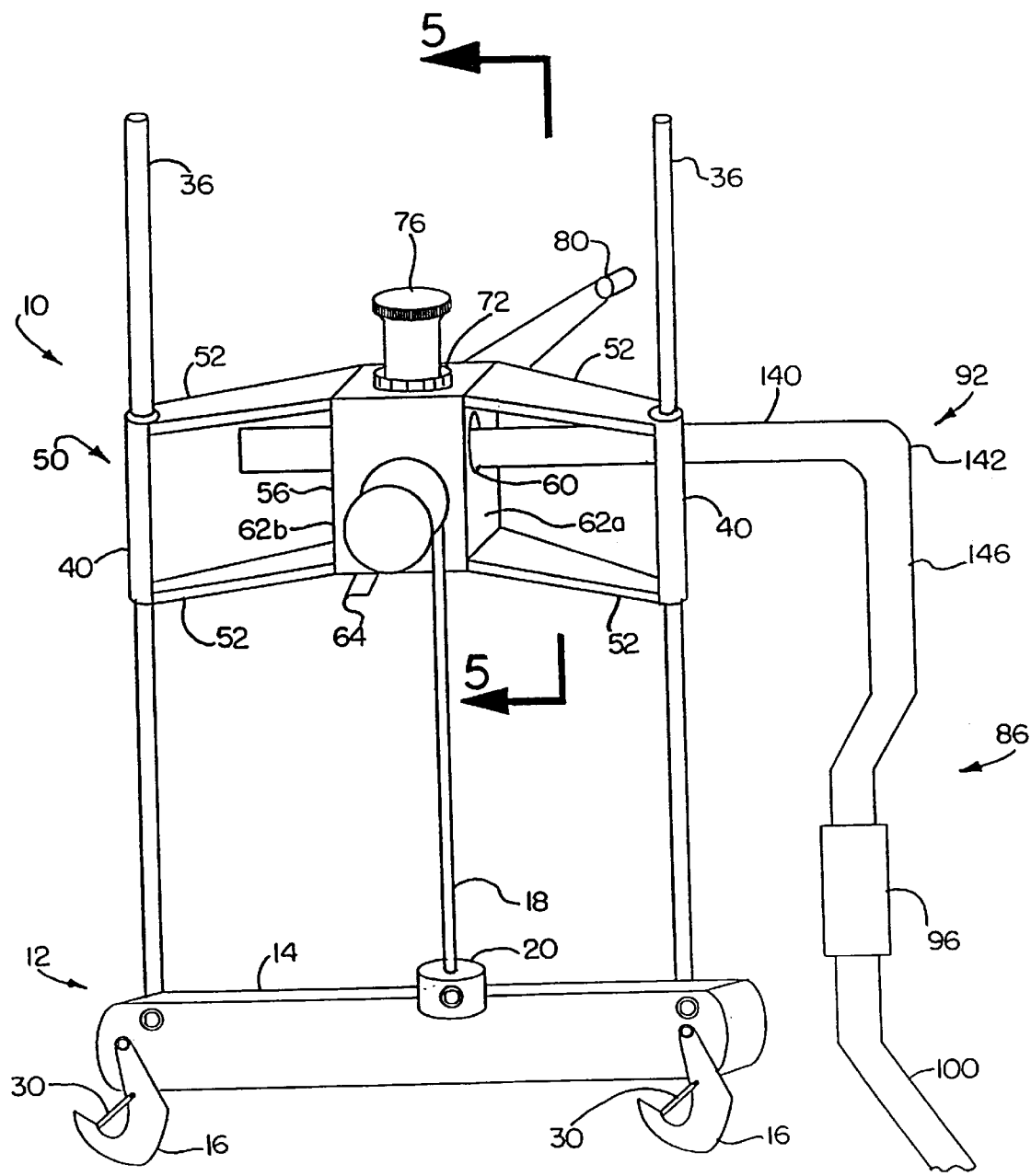
FIG. 2 is an enlarged perspective view of a sliding apparatus of the support apparatus according to the present invention.
Figure 5:
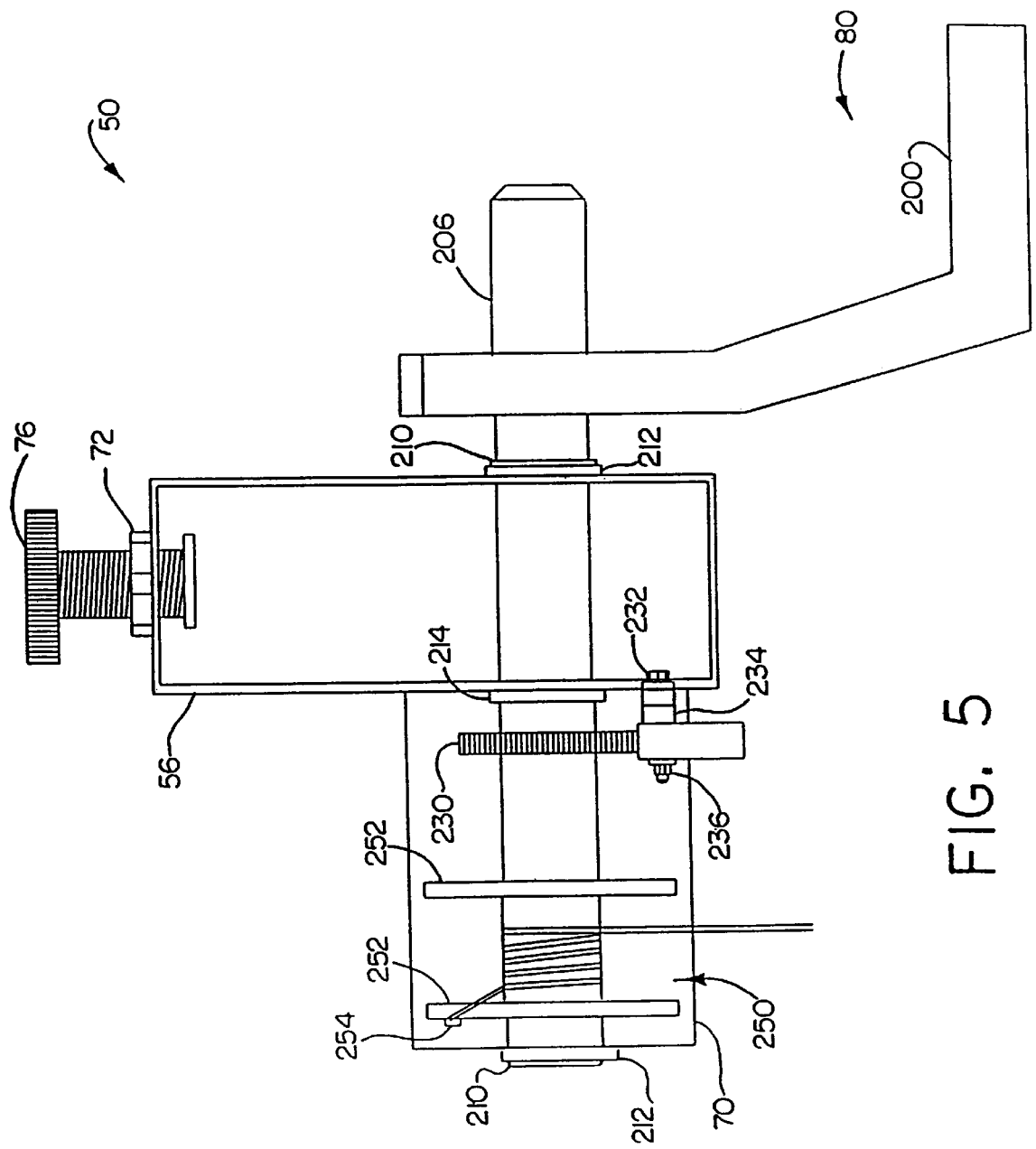
FIG. 5 is a partial side elevational view of the slide assembly in accordance with the present invention.

Turning now to FIG. 5, a partial cross-sectional view of the slide assembly 50 is shown taken a cross-section arrows A (FIG. 2). The slide bolt 76 is shown at the top of the slide assembly housing 56. The slide bolt 76 is threaded and screws into the slide assembly housing 56 via threaded sleeve 72 which is integral to the top of the slide assembly housing 56.

The cord crank 80 includes a crank handle 200 which facilitates easy turning of the cord crank 80. The crank handle 200 is coupled to a crank 206. The crank 206 runs completely through slide assembly housing 56 and cord assembly 70. Bearing rings 210, 212, 214 provide for easy turning of the crank rod within the slide assembly housing 56 and cord assembly 70.

A toothed gear 230 is coupled integrally around a portion of the crank rod 206 that lies within the cord assembly 70. The gear 230 serves to facilitate locking the crank rod 206 in a fixed position. The gear lever 64 is spring biased (not shown) to lock the crank rod 206 into a fixed position. The gear lever 64 secures into a space between two teeth of the gear 230. The gear lever 64 is fixedly attached to the slide assembly housing 56 via the bolt 232, bearing ring 234 and nut 236.

Thus, when the crank rod 206 has been rotated to a desired position (i.e. the hanger rod 140 is at a desired vertical position) a user can secure the position by engaging the gear lever 64 with the teeth of the gear 230. Likewise, when a user desires to effect rotation of the crank rod 206 via turning the crank handle 200, the gear lever 64 is first disengaged from the teeth of the gear 230.

A spool wheel 250 is coupled around the end of the crank rod 206 within the cord assembly 70. The cord 18 is fixedly attached to one of the wheels 252 of the spool wheel 250 by a cord fastener 254. The spool wheel 250 serves to contain the cord 18 within the wheels 252 of the spool wheel 250 as the cord 18 is wound and unwound along the crank rod 206 as it is rotated.

Referring now to FIGS. 1–5, the operation of the arm holder 10 will be described. A patient (not shown) is placed on the operating table 55. A limb of the patient is secured in a holding apparatus such as a sling 32 or sleeve or rings, for example. The hook bar 14 is attached to whatever apparatus is used for securing the limb. The hooks 16 are employed to effect attachment of the hook bar 14 to the holding apparatus.

Once the limb is attached to the hook bar 14, the limb can be raised by turning the crank handle 200 so as to rotate the crank rod 206 which in turn results in drawing in of the cord 18 into the cord assembly 70. As the cord 18 is drawn in, the hook bar 14 is raised thus raising the limb suspended in the sling 32. Additionally, the slide rods 36 serve to maintain the limb in a relatively fixed position and effect a smooth raising of the limb since the cord 18 is attached at the center of the hanger bar 14. Without the slide rods 36 and slide tubes 40, the limb would not be well balanced and could teeter back and forth while being raised. The slide rods 36 in conjunction with the slide tubes 40 provide for balancing the hanger bar 14 and affording for a smooth, steady raising and lowering of the hanger bar 14 and thus the limb. The crank handle 80 is turned until the limb is at a desired elevation. Once the limb is at the desired elevation, the gear lever 64 is engaged to lock the cord 18 in the manner described above. It will be appreciated that although the present invention has been described with respect to a mechanical crank handle 80 and mechanical gear lever 64 for raising the support assembly 12, it is understood that any suitable means for vertically raising and lowering the support assembly 12 falls within the scope of the present invention. For example, a motor with an electrical switch could be employed to effect raising and lowering of the support apparatus.

The limb can be horizontally positioning by sliding the slide assembly 50 along the horizontal portion 140 of the hanger bar 92. Once the slide assembly 50 is at a desired horizontal position along the horizontal portion 140, the slide bolt 76 can be turned to tighten against the horizontal portion 140 and thus secure the slide assembly 50. Thus, the slide assembly 50 affords the surgeon or other operating personnel to horizontally position the limb during the surgical procedure without having to touch the limb or the sling 32.

The limb can also be positioned along a horizontal plane by rotating the hanger bar 92 relative to the support bar 100. Accordingly, since tuning of the position of the limb can be effected in order to maximize work space during the surgical procedure.

It is to be understood that any combination of the support assembly 12, slide assembly 50 and support bar 86 may be employed to universally position the limb during a surgical procedure. It will also be appreciated that once a desired position is obtained, the limb can be maintained in a fixed position. Moreover, the support apparatus 10 affords for quick and easy repositioning of the limb if so desired.

Figure 6:
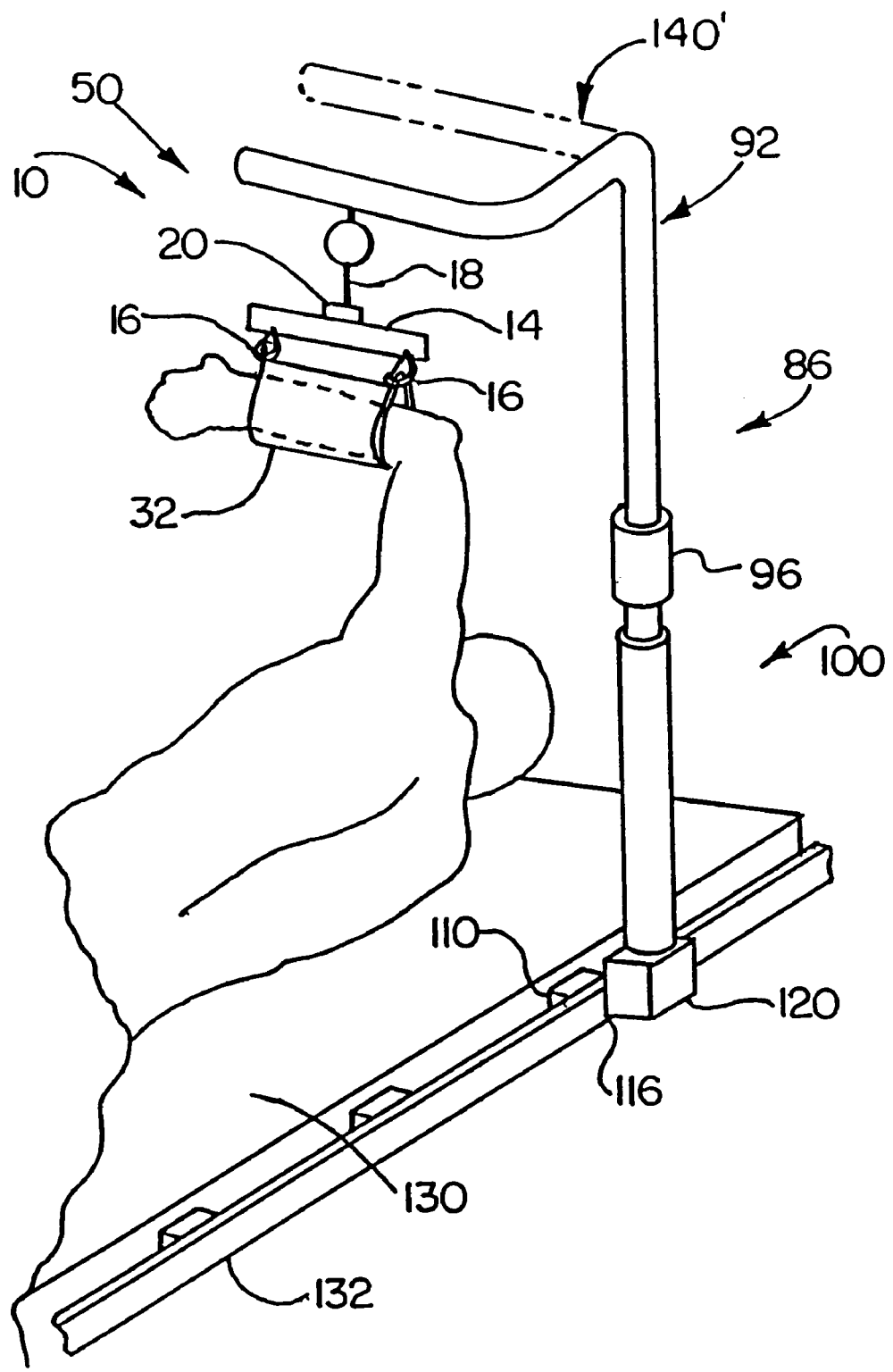
FIG. 6 is a schematic illustration of a modified support apparatus in accordance with another embodiment of the invention.

In an alternate embodiment schematically illustrated in FIG. 6, the horizontal portion 140' of the hanger bar 92 is bent or curved toward the patient's feet. This arrangement may provide additional space or a different availability of space for operating personnel during surgery.

Although the invention has been shown and described with respect to certain preferred embodiments, it is obvious that equivalents and modifications will occur to others skilled in the art upon the reading and understanding of the specification. The present invention includes all such equivalents and modifications, and is limited only by the scope of the following claims.

What is claimed is:

1. A surgical support apparatus for a limb of a patient comprising:

a support assembly for supporting the limb; and a mounting assembly slidably coupled to the support assembly by at least one slide rod and at least one slide tube; wherein the surgical support apparatus provides for vertical positioning of the limb, horizontal positioning of the limb, and rotatable positioning of the limb about a vertical axis; and wherein the mounting assembly further includes a cord assembly coupled to a crank operative to release and recoil the cord in order to vertically position the slide assembly relative to the mounting assembly and to provide for controlled vertical positioning of the limb.

2. The surgical support apparatus of claim 1 wherein the mounting assembly further includes a slide assembly, the slide assembly being horizontally positionable along a hanger bar so as to provide for horizontal positioning of the support assembly to effect horizontal positioning of the limb.

3. The surgical support apparatus of claim 1, wherein the mounting assembly further includes a support structure, the support structure including a first portion vertically coupled to a second portion, the first portion being horizontal rotatable relative to the second portion so as to provide for rotatable positioning of the limb along a horizontally plane.

4. The surgical support apparatus of claim 3, wherein the support structure includes an adjustable clamp adapted to mount the support apparatus to an operating table.

5. The surgical support apparatus of claim 3, wherein the support apparatus is floor mounted.

6. The surgical support apparatus of claim 3, wherein the support apparatus is wall mounted.

7. The surgical support apparatus of claim 1, the cord assembly including a windable cord adapted to be secured to the support assembly.

8. The surgical support apparatus of claim 7, the support assembly further including a horizontally disposed hook bar for securing the limb, the cord being attached to the hook bar.

9. The surgical support apparatus of claim 8, the support assembly further including a sling attached to the hook bar for holding the limb.

10. The surgical support apparatus of claim 1 being used in transaxillary first rib resection surgery.

11. A surgical support apparatus for a limb of a patient comprising:

a support assembly for supporting the limb; and a mounting assembly slidably coupled to the support assembly by at least one slide rod and at least one slide tube; wherein the surgical support apparatus provides for vertical positioning of the limb, horizontal positioning of the limb, and rotatable positioning of the limb about a vertical axis; wherein the mounting assembly further includes a cord assembly adapted to vertically position the slide assembly relative to the mounting assembly; and wherein the cord assembly is coupled to a crank operative to release and recoil the cord in order to provide for controlled vertical positioning of the limb.

12. A method for supporting and positioning a patient's body part during surgery comprising the steps of:

attaching the body part to a support assembly;

using a mounting assembly slidably coupled to the support assembly to position the body part, the mounting assembly being able to position the body part in at least the following manners: vertically, horizontally and rotatably about a vertical axis; wherein the step of using a mounting assembly includes a step of operating a crank to release and recoil a cord assembly to vertically position the mounting assembly and to provide controlled vertical positioning of the limb.

13. The method of claim 12 further including the step of horizontally positioning the limb via a slide assembly that is part of the mounting assembly, the slide assembly being horizontally positionable along a hanger bar.

14. A surgical support apparatus for holding and elevating a body part during surgery comprising:

a support assembly for supporting the limb; and a mounting assembly slidably coupled to the support assembly by at least one slide rod and at least one slide tube, the support assembly being vertically positionable relative to the mounting apparatus, the mounting assembly also including a slide assembly and a support structure, the slide assembly being horizontally positionable along a hanger bar so as to provide for horizontal positioning of the support assembly to effect horizontal positioning of the limb, the support structure including a first portion vertically coupled to a second portion, the first portion being horizontal rotatable relative to the second portion so as to provide for rotatable positioning of the limb about a vertical axis; and wherein the mounting assembly further includes a cord assembly coupled to a crank operative to release and recoil the cord in order to vertically position the slide assembly relative to the mounting assembly and to provide for controlled vertical positioning of the limb.

* * * * *